(12) United States Patent
Nishizono

(10) Patent No.: US 6,463,805 B1
(45) Date of Patent: Oct. 15, 2002

(54) APPARATUS AND METHOD FOR MEASURING DEFECT OF SAMPLE

(75) Inventor: Shigeo Nishizono, Tokyo (JP)

(73) Assignee: Mitsubishi Denki Kabushiki Kaisha, Tokyo (JP)

(*) Notice: Subject to any disclaimer, the term of this patent is extended or adjusted under 35 U.S.C. 154(b) by 16 days.

(21) Appl. No.: 09/694,027

(22) Filed: Oct. 23, 2000

(30) Foreign Application Priority Data

Feb. 25, 2000 (JP) ........................................ 2000-048664

(51) Int. Cl.[7] ................................................ G01M 7/00
(52) U.S. Cl. ............................................................ 73/663
(58) Field of Search ............................ 73/663, 597, 570

(56) References Cited

U.S. PATENT DOCUMENTS 4,631,963 A * 12/1986 Sprunt et al. ................. 73/597
5,083,463 A * 1/1992 Marshall et al. .............. 73/663

FOREIGN PATENT DOCUMENTS

JP         7-113791         5/1995

* cited by examiner

*Primary Examiner*—Richard A. Moller
(74) *Attorney, Agent, or Firm*—McDermott, Will & Emery

(57) ABSTRACT

In an apparatus comprising an inspection jig 10 including a sample mounting portion 11 for mounting a sample 1, a vibrator 22 for applying vibration to the sample 1 and a sound collector 20 for collecting a vibration sound when the vibration is applied to the sample 1 by the vibrator 22, and a sound detector 30 for conducting frequency analysis of the vibration sound collected by the sound collector 20, the defects of the sample are determined by sampling and analyzing the vibration sound when the vibration is applied to the sample 1 by the vibrator 22 on the time series.

8 Claims, 8 Drawing Sheets

APPLIED POINT

NON-DEFECTIVE ARTICLE

WAVEFORM VIBRATES IN MINUS REGION

DEFECTIVE ARTICLE

WAVEFORM VIBRATES IN PLUS REGION

DEFECTIVE ARTICLE

WAVEFORM VIBRATES IN PLUS AND MINUS REGIONS

APPARATUS AND METHOD FOR MEASURING DEFECT OF SAMPLE

BACKGROUND OF THE INVENTION

1. Field of the Invention

This invention relates to an apparatus for measuring defects such as substrate fractures or internal cracks in relation to samples such as material substrates (photo-voltaic cell, polycrystalline silicon substrate).

2. Description of the Related Art

Conventionally, there is an apparatus disclosed in, for example, JP-A-7-113791 as a measuring apparatus for speedily objectively evaluating uniformity of samples without damaging samples such as material substrates.

FIG. 9 is a block diagram showing a uniformity measuring apparatus of the samples. This measuring apparatus comprises a vibrator 102 for applying vibration to the end of a flat plate sample 101, a first vibration sensor 103 which is spaced a predetermined distance away from the applied vibration portion of the vibrator 102 and detects the vibration transferring the sample 101, and a second vibration sensor 104 which is spaced a predetermined distance away from the vibration sensor 103 and detects the vibration transferring the sample 101.

The vibration applied by the vibrator 102 is transferred from the applied vibration portion of the sample 101 to the other end direction and is detected by the first and second vibration sensors 103 and 104. Vibration detection signals detected by the first and second vibration sensors 103 and 104, respectively, are fed to filters 105 and 106 for eliminating noise signals and selecting a signal with a predetermined frequency, and are amplified by amplifiers 107 and 108. The detection signal from the vibration sensor 103 is fed to a terminal of a channel 1 of an oscilloscope 109 and the detection signal from the second vibration sensor 104 is fed to a terminal of a channel 2 of the oscilloscope 109 and the detection signals are respectively displayed. Then, uniformity of the sample 101 can be evaluated by calculating a difference in vibration transfer time or a difference in transfer speed based on each of the detection signals displayed on the oscilloscope 109.

The conventional apparatus as described above employs a method for evaluating uniformity using the transfer time and the transfer speed of the vibration to the sample. That is, this determination method is a method for analyzing the difference in instantaneous data between two points (the difference in transfer time, the difference in transfer speed) rather than change with time to determine uniformity, fractures or cracks of the sample by calculation, so that enough results could not be obtained for detection of fractures and internal cracks of the point fixing the sample, detection of defects (fractures or internal cracks) of the distant point or the point equal from two points in a vibration transfer area inside the sample, and detection of fine microcracks.

SUMMARY OF THE INVENTION

The invention is implemented to solve such problems, and it is an object of the invention to be able to detect defects of a sample irrespective of size and place of the defects (fractures or internal cracks of a material substrate) of the sample while enabling objective evaluation without doing damage to the sample.

According to the invention, there is provided an apparatus for measuring defects of a sample, comprising an inspection jig including a sample mounting portion for mounting the sample, a vibrator for applying vibration to the sample and a sound collector for collecting a vibration sound when the vibration is applied to the sample by this vibrator, and a sound detector for conducting frequency analysis of the vibration sound collected by the sound collector, and the defects of the sample are determined by sampling and analyzing an applied vibration sound when the vibration is applied to the sample by the vibrator on the time series.

In the invention, the vibration sound collected by the sound collector is respectively amplified through a low-pass filter and a high-pass filter of the sound detector and then differential calculation is made and also, a composite wave is outputted to an oscilloscope.

In the invention, a fixing part for fixing the sample of the sample mounting portion is made of a cushioning material and the sample mounting portion is mounted on a shaft of an inspection jig fixation side through a bearing.

In the invention, the sample is resiliently pinched and fixed by the sound collector and the fixing part of the sample mounting portion.

According to a second aspect of the invention, there is provided a method for measuring defects of a sample, comprising the steps of applying vibration to the sample mounted in a sample mounting portion by a vibrator, collecting a vibration sound when the vibration is applied to the sample by this vibrator on the time series by a sound collector, and determining the defects of the sample by conducting frequency analysis of the vibration sound collected by the sound collector.

In the invention of claim 6, after the first determination of the defects of the sample is made, the sample rotated a predetermined angle is fixed and again, vibration is applied to the sample by the vibrator and the defects of the sample are determined.

DETAILED DESCRIPTION OF THE PRESENT INVENTION

The present invention will be described with reference to the accompanying drawings.

First Embodiment

Figure 1A:
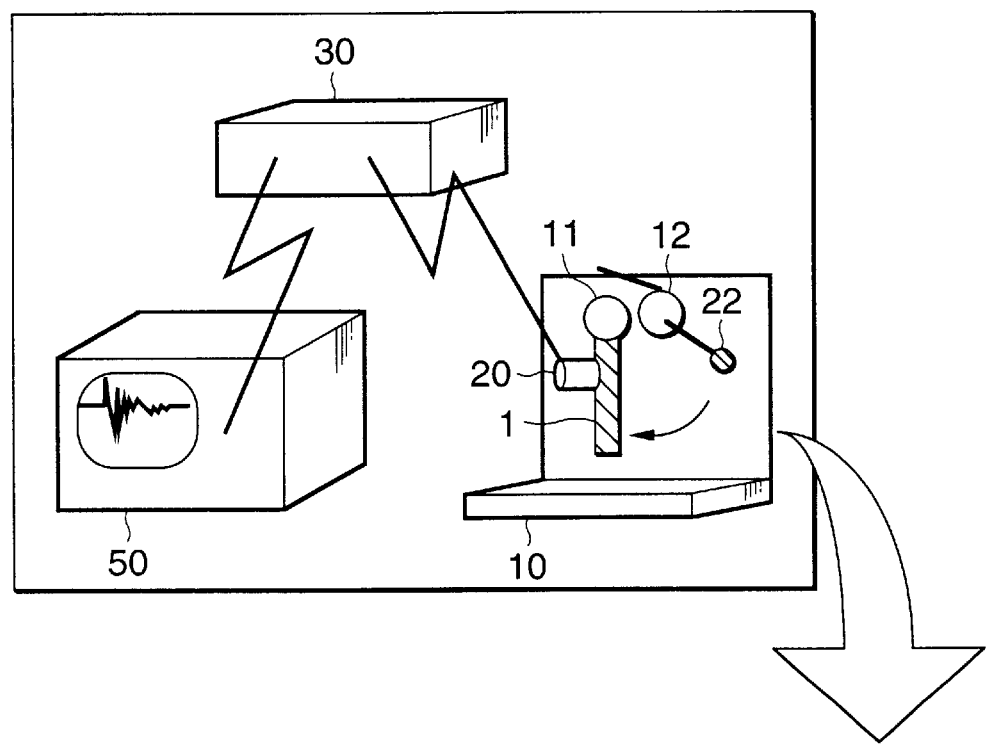
FIGS. 1A and 1B are illustrations showing a defect measuring apparatus of a sample according to a first embodiment of this invention.
Figure 1B:
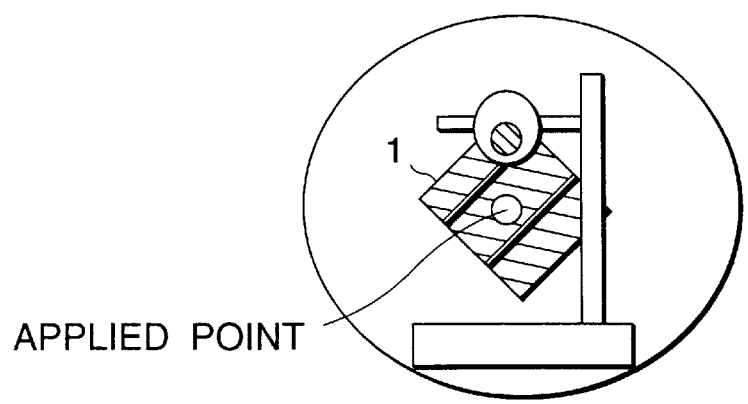

FIGS. 1A and 1B are illustrations showing a defect measuring apparatus of a sample according to a first embodiment of this invention, and FIG. 1A is a schematic configuration view showing all of the defect measuring apparatus and FIG. 1B is a side view showing an inspection jig of the defect measuring apparatus. The defect measuring apparatus of the sample according to the first embodiment comprises an inspection jig 10 for applying vibration by a vibrator 22 with a sample 1 such as a material substrate fixed and collecting the applied vibration sound by a sound collector 20 such as a capacitor microphone, a sound detector 30 for amplifying the vibration sound collected by the sound collector 20 through an LPF (low-pass filter) and a HPF (high-pass filter) and then calculating to output it as a composite wave, and an oscilloscope 50 for displaying a waveform calculated by the sound detector 30 and determining defects of the sample by the waveform.

Figure 2:
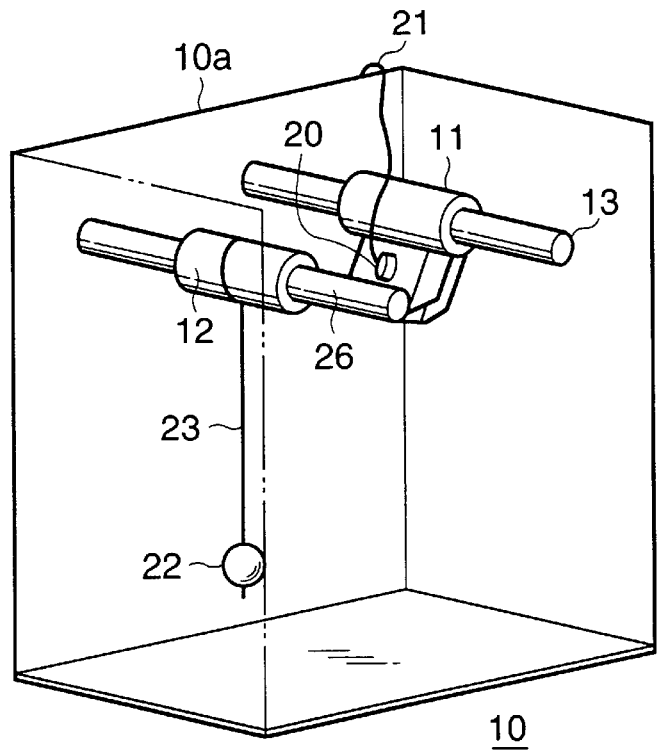
FIG. 2 is a perspective view showing the whole configuration of an inspection jig according to the first embodiment.
Figure 3:
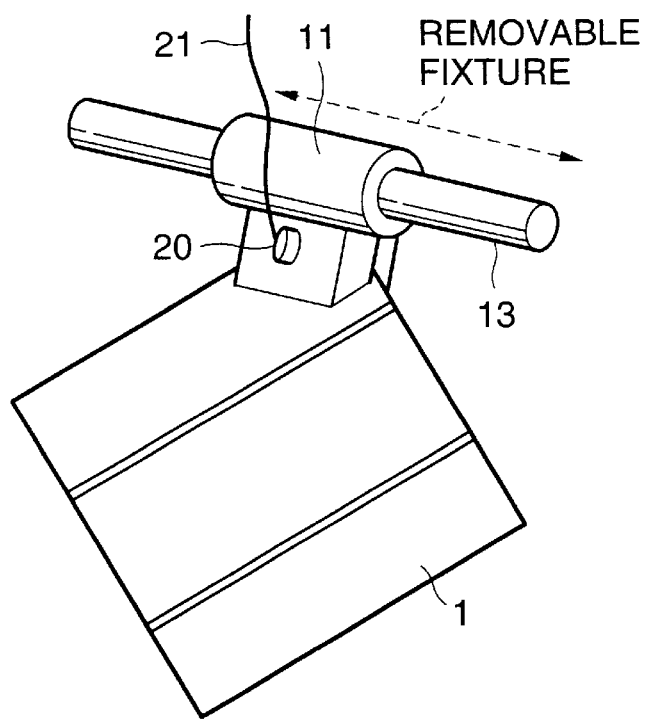
FIG. 3 is a perspective view showing a sample mounting portion of the inspection jig according to the first embodiment.

FIG. 2 is a perspective view showing the whole configuration of the inspection jig 10 of the embodiment. In FIG. 2, the inspection jig 10 mainly comprises a sample mounting portion 11 for mounting the sample 1, and a vibrator mounting part 12 for mounting the vibrator 22. As shown in FIG. 3, the sample mounting portion 11 is slidably and removably mounted on a shaft 13 provided in an inspection jig fixation side 10a through a bearing. Also, the vibrator mounting part 12 is slidably mounted on a shaft 26 provided in the inspection jig fixation side 10a through a bearing and mounts the vibrator 22 through a suspension wire 23 (for example, copper wire).

Figure 4:
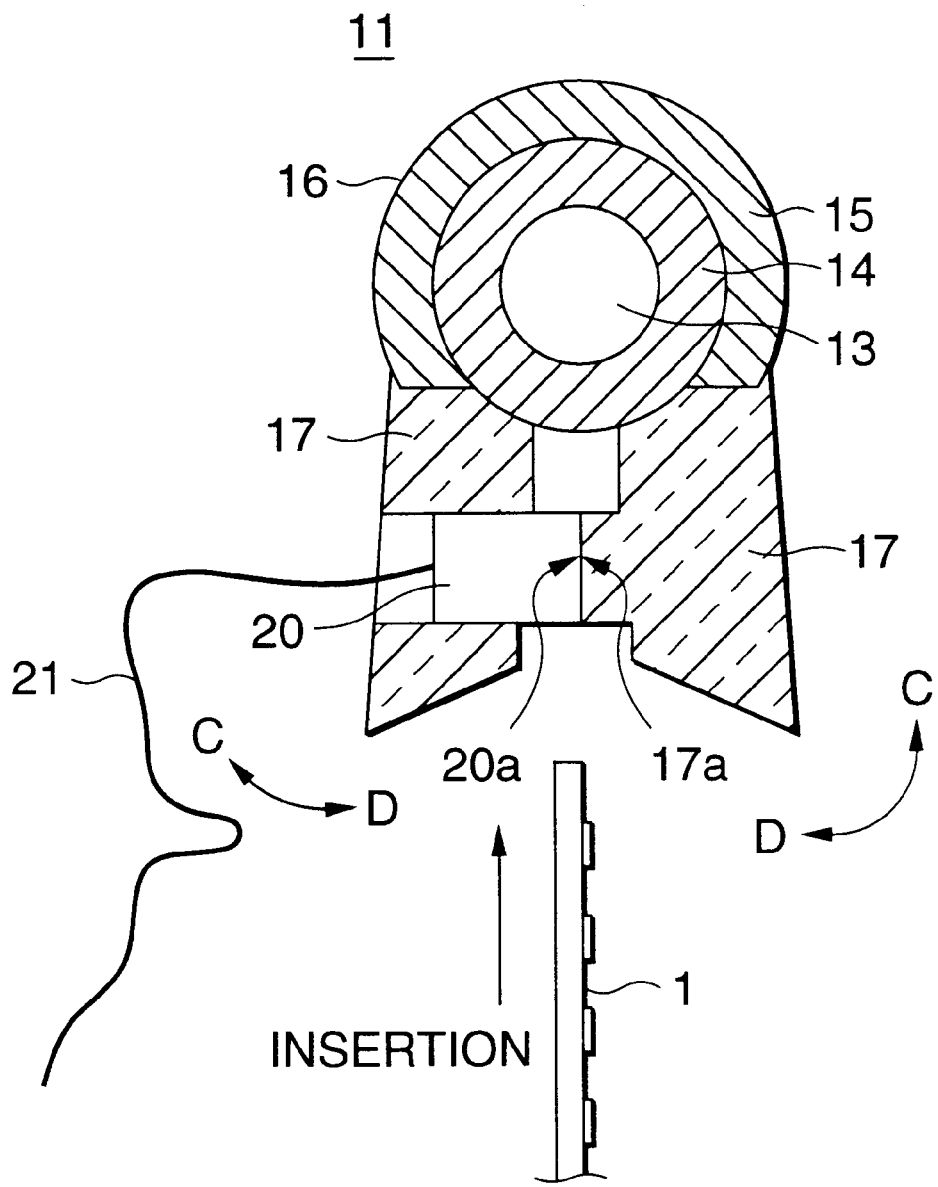
FIG. 4 is a sectional view showing the sample mounting portion of the inspection jig according to the first embodiment.

FIG. 4 is a sectional view showing details of the sample mounting portion 11 of the inspection jig 10. In FIG. 4, the sample mounting portion 11 comprises a bearing 14 slidably mounted on the shaft 13 of the inspection jig fixation side 10a, a protective part 15 provided so as to surround this bearing 14, a sample fixing part 17 (having cushion effect) such as PE light for fixing the sample 1, and a metal plate 16 placed so as to cover the protective part 15 and the sample fixing part 17. The sound collector 20 such as a capacitor microphone is mounted in a hole provided in a part of the sample fixing part 17. Then, the sample 1 is pinched and fixed by a contact surface 20a of the sound collector 20 and a fixing part contact surface 17a with the same area as this contact surface 20a. The metal plate 16 enables the sample 1 to be inserted into the sample fixing part 17 by opening the metal plate 16 in the direction of C shown in FIG. 4 and enables the sample 1 to be stably supported in the sample fixing part 17 by resiliently returning the metal plate 16 in the direction of D shown in FIG. 4.

Also, when the sample 1 is fixed in the sample fixing part 17, the contact surface 20a of the sound collector 20 is contacted on the surface having small unevenness of the sample 1, for example, the rear of the material substrate. As a result of this, collection of the applied vibration sound by the sound collector 20 can more be ensured to reduce a detection error.

Figure 5:
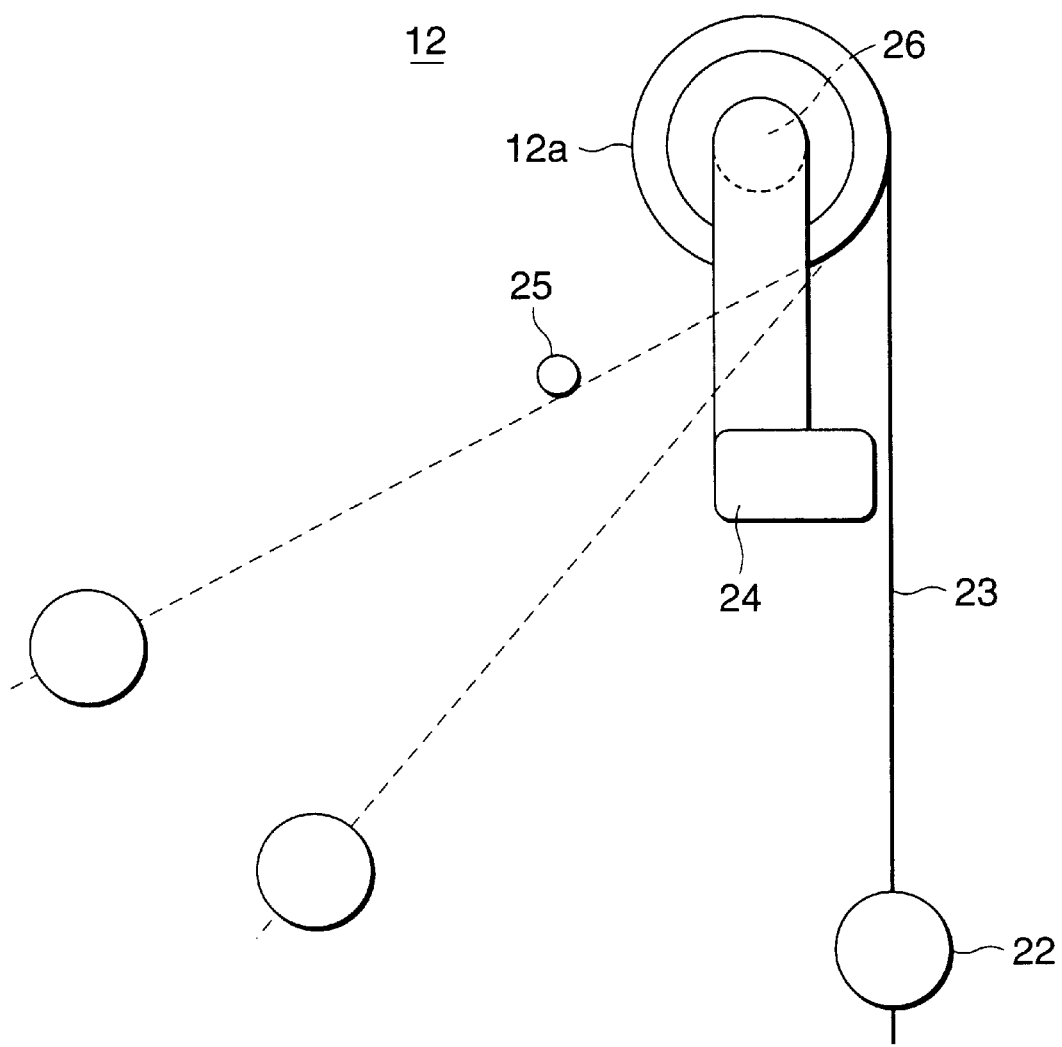
FIG. 5 is a side view showing a vibrator mounting part of the inspection jig according to the first embodiment.

FIG. 5 is a side view showing details of the vibrator mounting part 12 of the inspection jig 10. In FIG. 5, a vibrator mounting body 12a is slidably mounted on the shaft 26 provided in the inspection jig fixation side 10a through the bearing and mounts the vibrator 22 through the suspension wire 23 (for example, copper wire). A handle 24 of the vibrator mounting part 12 is means for adjusting the level of the vibrator 22 and the vibrator 22 is positioned so that the vibrator 22 collides with a predetermined applied point of the sample 1 mounted in the sample mounting portion 11. Also, a pole 25 for positioning provided in the inspection jig fixation side 10a plays a role in keeping a release point of the vibrator 22 constant.

Figure 6:
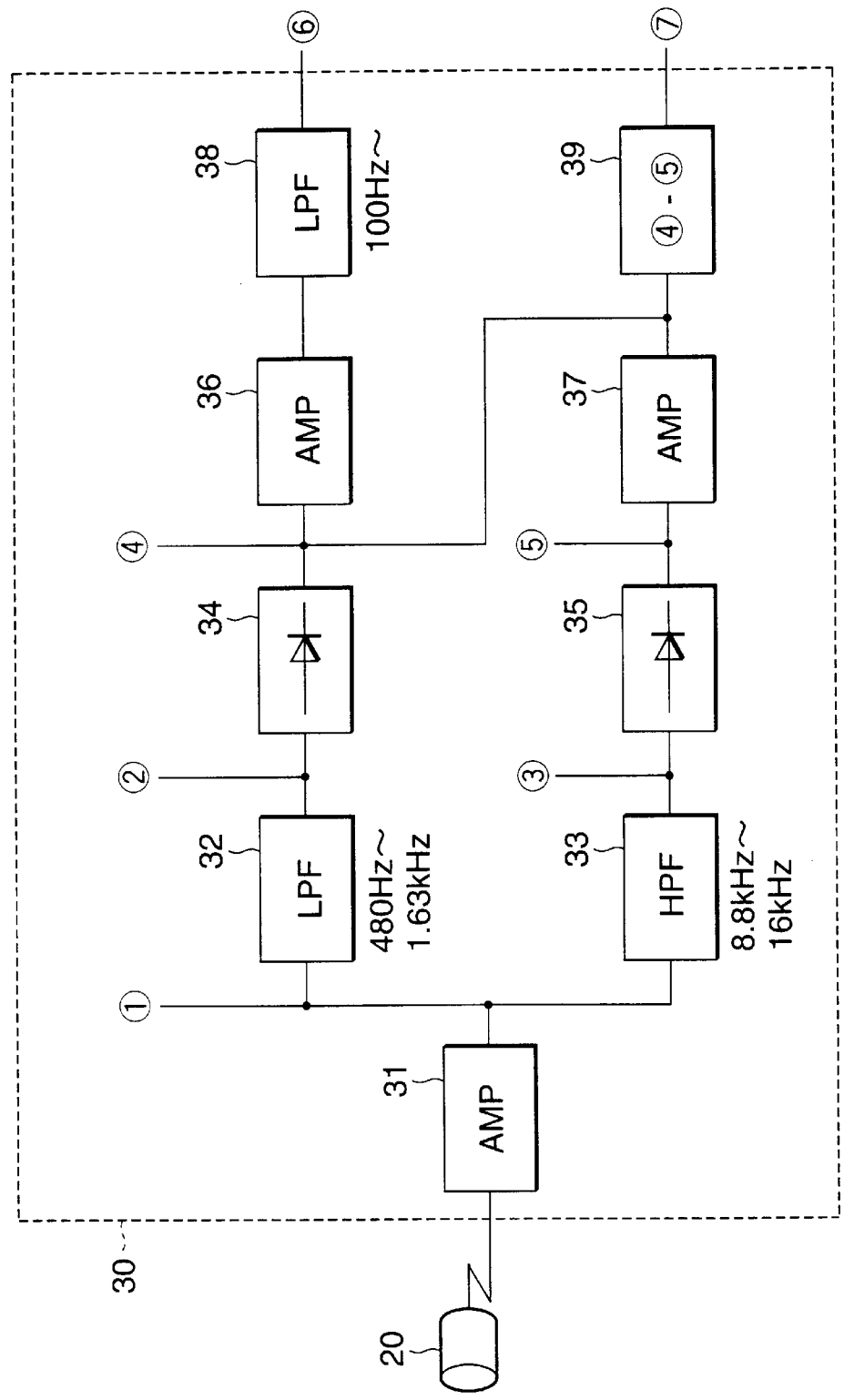
FIG. 6 is a circuit block diagram showing a sound detector according to the first embodiment.

FIG. 6 shows a circuit block diagram of the sound detector 30. The sound detector 30 sequentially collects the vibration sound collected by the sound collector 20 such as a capacitor microphone during a start of vibration to damping and convergence. That is, the vibration sound collected by the sound collector 20 is amplified by an amplifier 31, and then is fed to a low-pass filter (LPF) 32 and a high-pass filter (HPF) 33. Then, after the frequency is stratified by the LPF 32 and the HPF 33, the vibration sound is fed to rectifiers 34 and 35, respectively. After an output signal of the rectifier 34 is amplified by an amplifier 36, the signal is outputted to a terminal 6 through an LPF 38. Also, a signal amplifying an output signal of the rectifier 35 by an amplifier 37 is subtracted from the output signal of the rectifier 34 at a differential circuit 39 and the signal is outputted to a terminal 7.

A composite wave calculated by the sound detector 30 as described above is sequentially outputted to the oscilloscope 50. That is, the calculated results of the sound detector 30 are sequentially outputted to the oscilloscope 50 during a vibration start of the sample 1 to damping and convergence, and determine defects such as substrate fractures or internal cracks from a display region of the waveform.

Figure 7A:
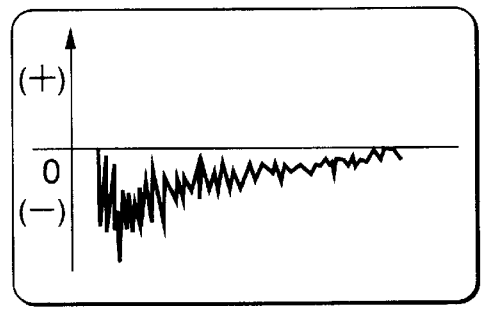
FIGS. 7A to 7C are graphs for determining defects of the sample from waveforms outputted to an oscilloscope according to the first embodiment.
Figure 7B:
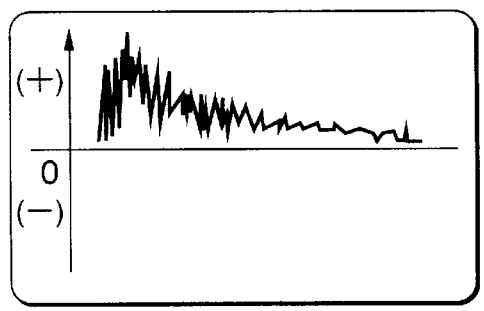
Figure 7C:
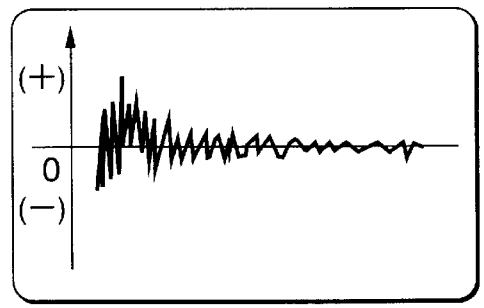

FIGS. 7A to 7C are graphs for determining defects of the sample from waveforms outputted to the oscilloscope 50. In the case of the embodiment, in a determination region of the defects of the sample, for a non-defective article (without fractures or internal cracks), the waveform vibrates to converge in only a minus region as shown in FIG. 7A. On the contrary, for a defective article (with fractures or internal cracks), the waveform vibrates to converge in only a plus region or in plus and minus regions as shown in FIGS. 7B and 7C. In this manner, calculations of the frequency are made. Incidentally, in FIGS. 7A to 7C, an axis of ordinate indicates amplitude of the composite wave and an axis of abscissa indicates time.

Figure 8:
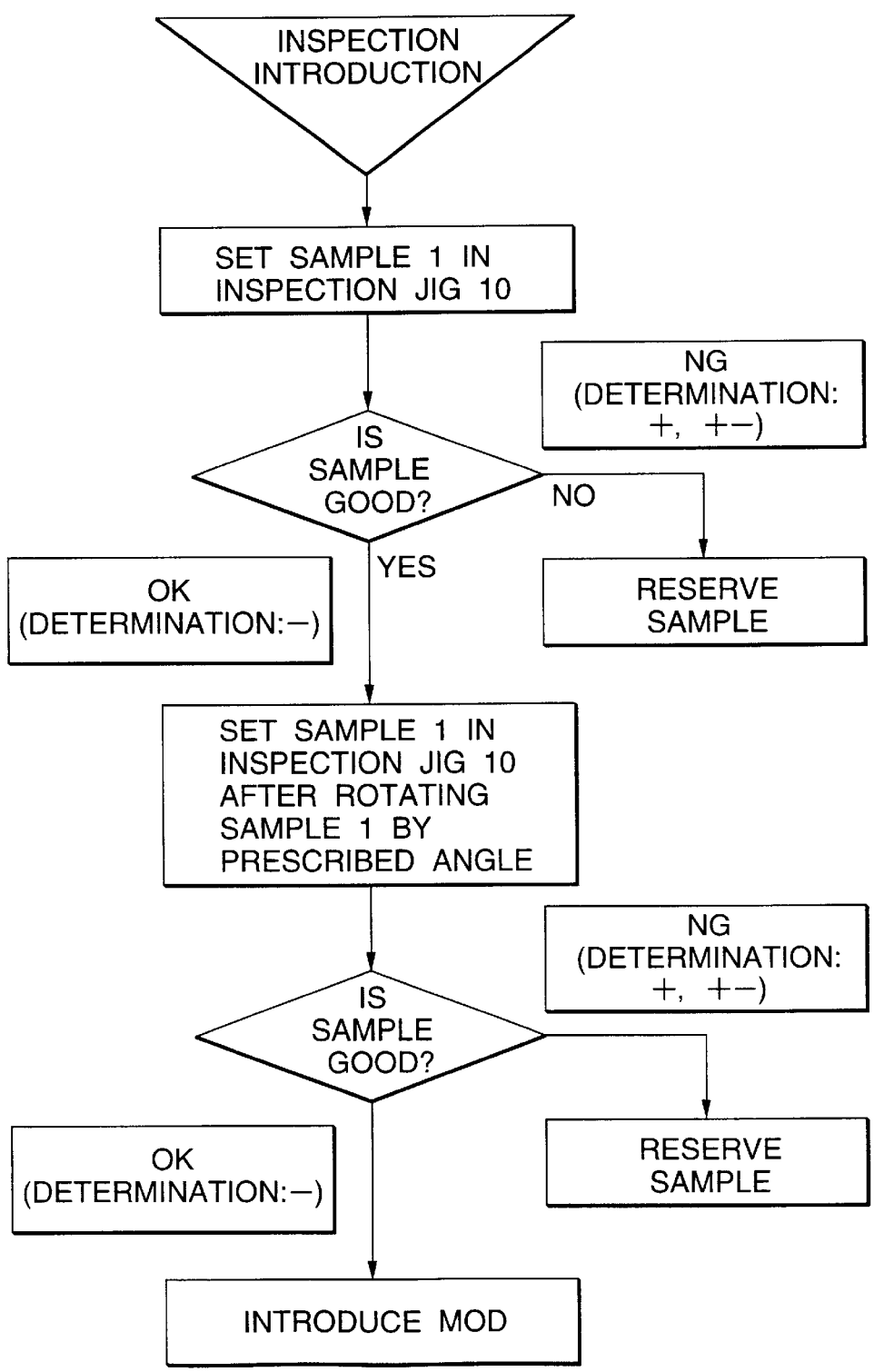
FIG. 8 is a flowchart determining the defects of the sample according to the first embodiment.
Figure 9:
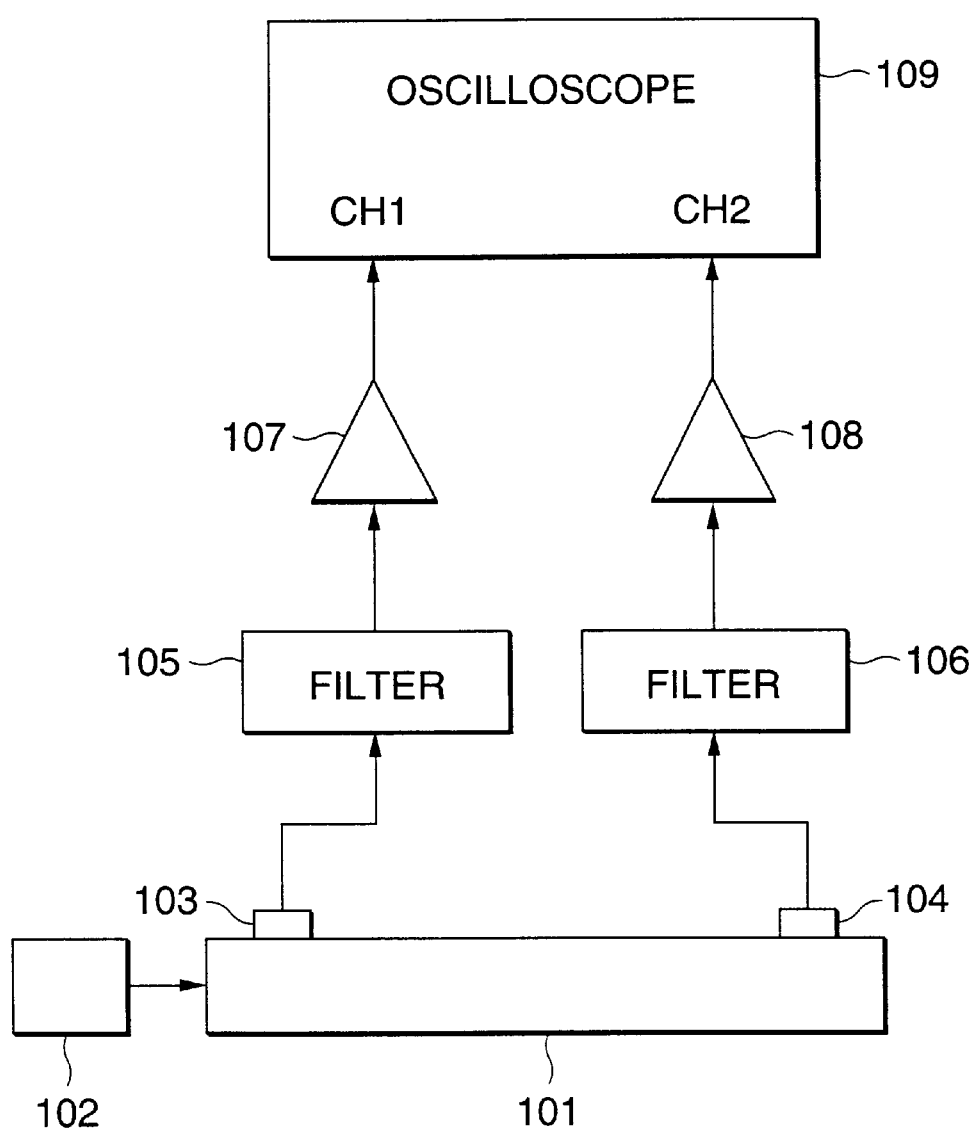
FIG. 9 is a block diagram showing a conventional uniformity measuring apparatus of a sample.

FIG. 8 is a flowchart showing operation procedure for improving accuracy of a method of determining the defects (fractures or internal cracks) of the sample described above. In FIG. 8, first, after the sample 1 is set in the inspection jig 10, vibration is applied to the sample 1 by the vibrator 22 and the vibration sound is collected by the sound collector 20 and is fed to the sound detector 30. In the sound detector 30, frequency analysis of the vibration sound obtained by the sound collector 20 is conducted and a composite waveform is outputted to the oscilloscope 50. An operator determines whether the sample is a non-defective article or a defective article by the graph of the FIGS. 7A to 7C. In this case, if the determination is the defective article (NG), the inspection operation is completed. Next, if the determination is the non-defective article, after the sample 1 is rotated a predetermined angle (for example, 180 degrees), the sample 1 is again set in the inspection jig 10. Then, vibration is applied to the sample 1 by the vibrator 22 and the vibration sound is collected by the sound collector 20 and further is analyzed in relation to the frequency by the sound detector 30 and a composite waveform is outputted to the oscilloscope 50. The operator again determines whether the sample is a non-defective article or a defective article by the graph of the FIGS. 7A to 7C. In this manner, it is determined that the sample is the non-defective article only when inspections of predetermined times (typically, two times) are OK.

According to the invention as described above, determination operations of defects such as fractures or internal cracks in relation to a sample such as a material substrate can be made efficient and accuracy of the defect determination can be improved and quality can be maintained without damage of the sample.

Particularly, according to the invention, the defects of the sample are determined by sampling and analyzing an applied vibration sound when vibration is applied to the sample by a vibrator on the time series, so that observation can be made on the time series during a start of a vibration waveform to damping and convergence, and it also becomes best suitable for detection of the defects of the point fixing the sample, detection of the defects of the distant point in a vibration transfer area inside the sample, and detection of fine cracks such as microcracks.

Also, according to the invention, the vibration sound collected by a sound collector is respectively amplified through a low-pass filter and a high-pass filter of a sound detector and then differential calculation is made and also a composite wave is outputted to an oscilloscope, so that the defects of the sample can be objectively determined.

Further, according to the invention, a fixing part for fixing the sample in a sample mounting portion is made of a cushioning material and the sample mounting portion is mounted on a shaft of an inspection jig fixation side through a bearing, so that the sample mounting portion is designed for movable type and sampling and observation can surely be made until damping and convergence of a detection waveform. Also, a shock when the vibration is applied to the sample can be minimized and damage is not caused to the sample.

Furthermore, according to the invention, the sample is resiliently pinched and fixed by the sound collector and the fixing part of the sample mounting portion, so that operations for setting (mounting) and resetting (removing) the sample in the sample mounting portion can be improved and the mounting operations of the sample can be semiautomated. Also, reproducibility of inspection can be improved by keeping fixed force of the sample constant.

According to the invention, after the first determination of the defects of the sample is made, the sample rotated a predetermined angle is fixed and again vibration is applied to the sample by the vibrator and the defects of the sample are determined, so that detection leakage of the defects of the sample can be eliminated.

What is claimed is:

1. An apparatus for measuring defects of a sample, comprising:
    an inspection jig comprising a sample mounting portion for mounting the sample, a vibrator for applying vibration to the sample, a sound collector for collecting a vibration sound when the vibration is applied to the sample by the vibrator; and
    a sound detector for conducting frequency analysis of the vibration sound collected by the sound collector,
    wherein the defects of the sample are determined by sampling and analyzing the vibration sound when the vibration is applied to the sample by the vibrator on the time series.

2. The apparatus as defined in claim 1, wherein the vibration sound collected by the sound collector is respectively amplified after the vibration sound passes through a low-pass filter and a high-pass filter of the sound detector, and
    differential calculation is then made and also a composite wave is outputted to an oscilloscope.

3. The apparatus as defined in claim 1, wherein a fixing part for fixing the sample in the sample mounting portion is made of a cushioning material and the sample mounting portion is mounted on a shaft of an inspection jig fixation side through a bearing.

4. The apparatus as defined in claim 1, wherein the sample is resiliently pinched and fixed by the sound collector and the fixing part of the sample mounting portion.

5. A method for measuring defects of a sample, comprising the steps of:
    applying vibration to the sample mounted in a sample mounting portion by a vibrator;
    collecting a vibration sound generated when the vibration is applied to the sample by the vibrator on the time series by a sound collector, and
    determining the defects of the sample by conducting frequency analysis of the vibration sound collected by the sound collector.

6. The method as defined in claim 5, further comprising the steps of:
    rotating the sample by a predetermined angle after the determination step of the defects of the sample is performed;
    fixing the sample to the sample mounting portion;
    applying the vibration to the sample by the vibrator when the vibration is applied to the sample by the vibrator on the time series;
    collecting a vibration sound by a sound collector generated when the vibration is applied to the sample by the vibrator on the time series, and
    determining the defects of the sample by conducting frequency analysis of the vibration sound collected by the sound collector.

7. The method as defined in claim 5, wherein said vibrator is suspended from a vibrator mounting part through a suspension wire, and further comprising the step of:
    colliding said vibrator with a predetermined applied point of said sample.

8. The method as defined in claim 5, wherein said sample mounting portion forms part of an inspection jig, and further comprising the steps of:
    conducting the frequency analysis of the vibration sound by a sound detector; and
    determining defects of the sample by sampling and analyzing the vibration sound when the vibration is applied to the sample by the vibrator on the time series.

* * * * *